United States Patent [19]

Toyoura et al.

[11] 4,408,083
[45] Oct. 4, 1983

[54] METHOD OF TREATING HYDROPEROXIDE MIXTURES

[75] Inventors: Masakazu Toyoura; Koichi Shomura, both of Iwakuni; Hirotoshi Tsuchida; Tadateru Murakami, both of Otake, all of Japan

[73] Assignee: Mitsui Petrochemical Industries, Ltd., Tokyo, Japan

[21] Appl. No.: 293,510

[22] Filed: Aug. 17, 1981

[30] Foreign Application Priority Data

Aug. 19, 1981 [JP] Japan .................................. 56-113028

[51] Int. Cl.³ .......................................... C07C 179/02
[52] U.S. Cl. .................................... 568/576; 568/385; 568/756; 568/798
[58] Field of Search ........................ 568/756, 576, 385

[56] References Cited

U.S. PATENT DOCUMENTS 4,120,902 10/1978 Wu ........................................ 568/576
4,230,890 10/1980 Burkholder ............................ 568/576
4,271,321 6/1981 Voges .................................... 568/576
4,293,720 10/1981 Iwaki .................................... 568/576

Primary Examiner—Werren B. Lone
Attorney, Agent, or Firm—Sherman & Shallowway

[57] ABSTRACT

Disclosed is a method of treating hydroperoxide mixtures, which comprises bringing an oily hydroperoxide mixture containing (A) an aromatic hydroperoxide having a hydroperoxymethyl group directly bonded to the aromatic nucleus and (B) an aromatic hydroperoxide having a 2-hydroperoxy-2-propyl group bonded directly to the aromatic nucleus into contact with an aqueous alkali solution, separating the aqueous phase from the oil phase and decomposing at least a part of the component (A) extracted in the aqueous phase.

According to this method, the starting oily hydroperoxide mixture can be converted to a mixture in which the primary hydroperoxide content is reduced without substantial loss of the tertiary hydroperoxide. Therefore, aromatic hydroperoxide mixtures suitable for production of phenols can advantageously be proceeded.

20 Claims, 2 Drawing Figures

METHOD OF TREATING HYDROPEROXIDE MIXTURES

BACKGROUND OF THE INVENTION (1) Field of the Invention:

The present invention relates to a method of reducing the aromatic primary hydroperoxide content in a hydroperoxide mixture containing an aromatic primary hydroperoxide and an aromatic tertiary hydroperoxide.

(2) Description of the Prior Art:

The method of producing phenols by acid-decomposing hydroperoxides obtained by liquid phase oxidation of alkyl aromatic compounds is industrially valuable as means for preparing phenol, cresol, hydroquinone and resorcin. Furthermore, the above-mentioned hydroperoxides are valuable as the starting compounds for production of peroxides or aromatic alcohols. When a compound having at least two different alkyl groups is used as the alkyl aromatic compound in the above-mentioned liquid phase oxidation, there is often formed a mixture of at least two hydroperoxides having the respective alkyl groups converted to hydroperoxides. If this mixture is directly used as the starting material for the production of phenols, undesirable compounds are formed or the reaction is adversely influenced, resulting in various disadvantages.

For example, in the liquid phase oxidation of cymene, there are formed a primary hydroperoxide based on the oxidation of the methyl group and a tertiary hydroperoxide based on the oxidation of the isopropyl group. It is known that when cresol is prepared from a mixture containing both the hydroperoxides by acid decomposition, formaldehyde formed by acid decomposition of the primary hydroperoxide is condensed with formed cresol to form a resinous product, resulting in reduction of the yield of cresol. In order to eliminate this defect, it has been desired to selectively reduce or remove the primary hydroperoxide in the hydroperoxide mixture or to selectively convert the primary hydroperoxide to a compound having no bad influences. However, there has not been developed an industrial process metting this desire satisfactorily.

For example, a process in which the above-mentioned hydroperoxide mixture is directly reacted with a basic compound is proposed in U.S. Pat. No. 2,728,797 or Japanese Patent Publication No. 12183/77. However, even according to this proposal, it is impossible to sufficiently control decomposition of the tertiary hydroperoxide.

SUMMARY OF THE INVENTION

We made researches with a view to developing a method capable of overcoming the foregoing defects and disadvantages involved in the conventional techniques, and we found that the foregoing defects and disadvantages can effectively be moderated by adoption of a specific multistaged method comprising the extraction operation using an aqueous alkali solution and the alkali-decomposition operation.

More specifically, in accordance with the present invention, there is provided a method of treating hydroperoxide mixtures, which comprises bringing an oily hydroperoxide mixture containing (A) an aromatic hydroperoxide having an hydroperoxymethyl group directly bonded to the aromatic nucleus and (B) an aromatic hydroperoxide having a 2-hydroperoxy-2-propyl group bonded directly to the aromatic nucleus into contact with an aqueous alkali solution, separating the aqueous phase from the oil phase and decomposing at least a part of the component (A) extracted in the aqueous phase.

DETAILED DESCRIPTION OF THE PREFERRED EMBODIMENTS

Figure 1:
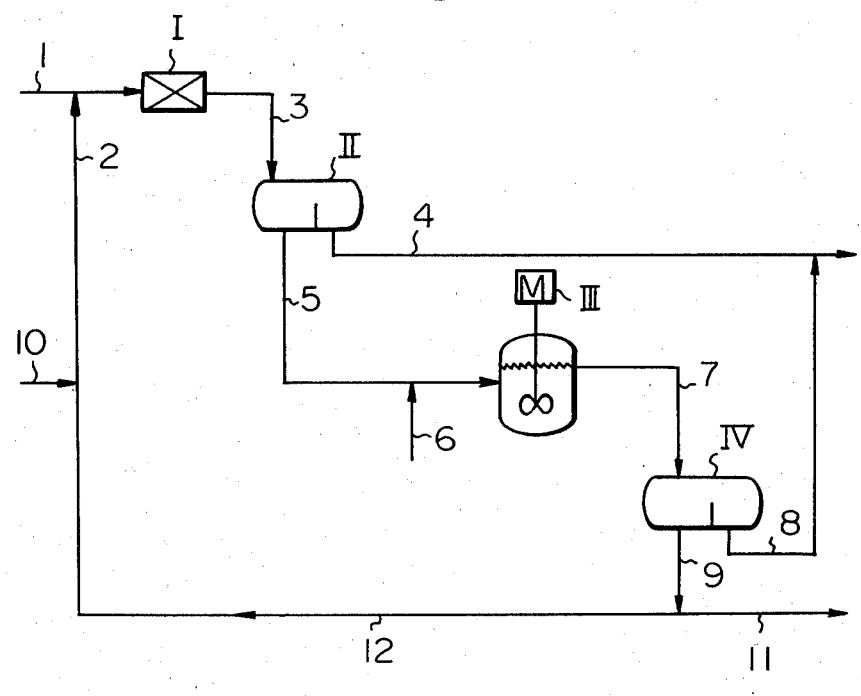
FIG. 1 is a diagram illustrating an embodiment of the apparatus to be used for carrying out the method of the present invention.

The aromatic hydroperoxide (A) having a hydroperoxymethyl group directly bonded to the aromatic nucleus is a compound represented by the following formula:

$$Ar-CH_2OOH$$

wherein Ar stands for a substituted or unsubstituted aromatic group.

As specific examples, the following compounds can be mentioned:

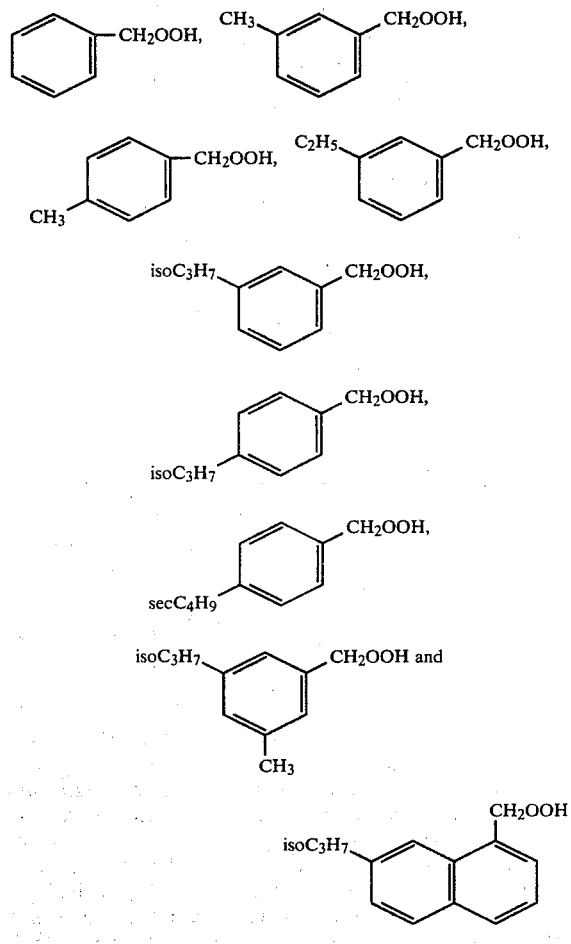

The aromatic hydroperoxide (B) having a 2-hydroperoxy-2-propyl group directly bonded to the aromatic nucleus is a compound represented by the following formula:

Ar'—C(CH₃)₂OOH

Wherein Ar' stands for a substituted or unsubstituted aromatic group.

As specific examples, the following compounds can be mentioned:

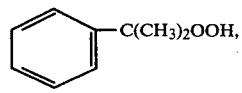

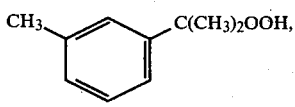

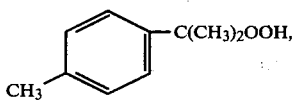

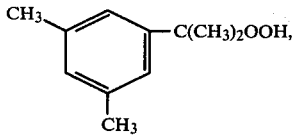

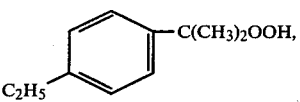

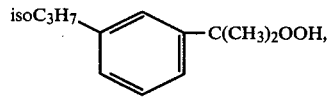

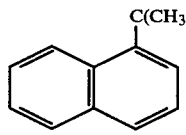

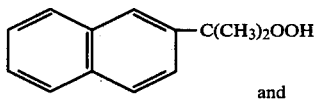

and

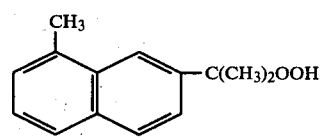

In the present invention, the mixing ratio of the hydroperoxides (A) and (B) is not particularly critical, but good results are ordinarily obtained when the treatment of the present invention is applied to a mixture containing 5 to 40 parts by weight, especially 10 to 30 parts by weight, of the hydroperoxide (A) and 95 to 60 parts by weight, especially 90 to 70 parts by weight, of the hydroperoxide (B) [the total amount of both the hydroperoxides is 100 parts by weight]. A typical instance of the above-mentioned mixture is a reaction product obtained by oxidizing an aromatic compound having methyl and isopropyl groups bonded to the aromatic nucleus in the liquid phase with molecular oxygen or a concentrate thereof. For example, there can be mentioned oxidation products of m-cymene, p-cymene, a mixture of m-cymene and p-cymene, 2,4-dimethylisopropylbenzene, 3,5-dimethylisopropylbenzene and 1-methyl-7-isopropylnaphthalene, and concentrates thereof.

It is preferred that the mixture of the hydroperoxides (A) and (B) be diluted with an aromatic hydrocarbon such as benzene, toluene, ethylbenzene, cumene, xylene, cymene, diisopropylbenzene or dimethylisopropylbenzene. When such diluent is used, it is preferred that the hydroperoxide concentration be adjusted to 1 to 40% by weight, especially 5 to 15% by weight.

The above-mentioned oxidation products of aromatic hydrocarbons having methyl and isopropyl groups or condensates thereof are ordinarily in the state diluted with the starting aromatic hydrocarbon.

The oxidation product may be either one oxidized in the non-aqueous state or one oxidized in the presence of an alkaline aqueous solution. In the latter case, the oxidation product is ordinarily used after separation and removal of the alkaine aqueous solution.

When an oily mixture containing the components (A) and (B) is brought into contact with an alkali aqueous solution, parts each of the components (A) and (B) are extracted in the alkali aqueous solutions. Usually, the ratio (A)/[(A)+(B)] in the starting oily mixture is smaller than the ratio (A)/[(A)+(B)] in the extract. Accordingly, the content of the component (A) in the extraction residue is lower than the content of the component (A) in the starting mixture.

It is preferred that the pH value of the alkali aqueous solution be at least 11 and especially 12 to 14. If the pH value is smaller than 11, the extraction efficiency is reduced. As the alkali aqueous solution, there are preferably used an aqueous solution of sodium hydroxide and an aqueous solution of potassium hydroxide. These aqueous solutions may comprise, dissolved therein, sodium carbonate or an organic acid salt, especially an aromatic organic acid salt such as sodium cuminate. The organic acid salt has an effect of enhancing the ratio of extraction of the hydroperoxides into the alkali aqueous solution. Therefore, it is preferred that such organic acid salt be contained in the alkali aqueous solution in the state dissolved therein.

In order to control decomposition of the tertiary hydroperoxide in the oil layer and enhance selective extraction of the primary hydroperoxide into the aqueous layer, it is preferred that the temperature adopted for contact with the alkali aqueous solution and oil-water separation be as low as possible. For example, a temperature of 0° to 40° C., especially 5° to 35° C., is preferred.

It is preferred that the alkali aqueous solution be used in an amount of 0.1 to 5 parts by volume, especially 0.2 to 1 part by volume, per part by volume of the oily hydroperoxide mixture. It is preferred that there should not be left a long time between the contact operation and the phase separation. Ordinarily, this time is 1 minute to about 2 hours. The extraction (contact operation) is ordinarily completed within 1 minute and especially within 0.2 minute.

After oil-water separation, the oil layer in which the primary hydroperoxide concentration has drastically been reduced is subjected to acid decomposition, if desired after concentration, whereby phenols can be obtained in high yields. The alkali aqueous solution phase contains the primary hydroperoxide and tertiary hydroperoxide in the state where the ratio of the primary hydroperoxide is made higher than in the starting oily hydroperoxide mixture. When this alkali aqueous solution phase is heated, the primary hydroperoxide is decomposed to an aldehyde such as cuminaldehyde and further to an alcohol such as isopropylbenzyl alcohol and a carboxylic acid such as cuminic acid. However, it is ordinarily preferred that the tertiary hydroperoxide be recovered as much as possible while preventing decomposition and be used together with the above-mentioned oil layer. From this viewpoint, it is often advantageous that the primary hydroperoxide is not completely decomposed but partially decomposed. More specifically, there may preferably be adopted such conditions that the total tertiary hydroperoxide decomposition ratio is lower than 4%, preferably lower than 3%, while the total primary hydroperoxide decomposition ratio is maintained at a level higher than 40%, preferably higher than 50%. These conditions can easily be realized by adjusting the decomposition time within the range described hereinafter according to the concentration of the alkali aqueous solution and the decomposition temperature.

The decomposition temperature is ordinarily in the range of from 20° to 100° C. and especially in the range of 20° to 80° C., and it is preferred that the decomposition temperature be higher than the temperature adopted for the above-mentioned extraction operation. The decomposition time is in the range of from 0.2 to about 100 minutes. At the decomposition step, in order to extract and recover the tertiary hydroperoxide from the decomposed mixture, a hydrocarbon, preferably an aromatic hydrocarbon, especially preferably the same hydrocarbon as contained in the starting oily hydroperoxide mixture, is made present in the alkali decomposition system in advance, and after the decomposition, the oil layer is recovered by two-phase separation. The so recovered oil layer contains the undecomposed tertiary hydroperoxide, and the decomposition products of the primary and tertiary hydroperoxides are mixed with the oil layer separated after contact with the alkali aqueous solution and are utilized as starting materials for production of phenols and the like.

The aqueous layer is separated and it is then mixed with a fresh alkali aqueous solution, and it is used again as the alkali aqueous solution for extraction. When the separated aqueous layer is neutralized and brought into contact with an appropriate extracting agent, organic compounds dissolving in the aqueous layer, such as carboxylic acids, can be recovered.

According to the present invention, the starting hydroperoxide mixture can be converted to a mixture having a reduced primary hydroperoxide content without substantial loss of the tertiary hydroperoxide. Therefore, a hydroperoxide mixture suitable as the starting material for production of phenols can advantageously be provided according to the present invention.

The present invention will now be described in detail with reference to the following Examples that by no means limit the scope of the invention.

EXAMPLE 1

The treatment of a product obtained by oxidation of cymene was carried out by using an apparatus shown in FIG. 1.

More specifically, 100 parts by volume of an oily reaction product obtained by air-oxidizing cymene in the presence of an alkali aqueous solution stabilizer and performing oil-water separation, which contained 16% by weight of cymene hydroperoxide (hereinafter referred to as CyHP) (tertiary CyHP/primary CyHP=86/14) and 80% by weight of cymene was supplied to an extractor I from a pipe 1 and 40 parts by volume of a sodium hydroxide aqueous solution containing a salt of an organic acid and having a pH value of 13.7 was simultaneously supplied to the extractor I. Both the liquids were sufficiently contacted with each other at 25° C. in the extractor I. The obtained mixture was transferred through a pipe 3 to a stationary tank II where oil-water separation was effected.

The water layer was withdrawn from a pipe 5 and is fed to a decomposition tank III provided with a stirrer together with 4 parts by volume of cymene supplied from a pipe 6, and decomposition was conducted at 60° C. for 25 minutes. Before the decomposition, 8.4 parts by weight of CyHP (tertiary CyHP/primary CyHP molar ratio of 64/36) and 2.5 parts of sodium hydroxide were contained in the water layer. By this decomposition operation, 56% of the total primary CyHP and 2.2% of the total tertiary CyHP were decomposed. Accordingly, the ratio of the total mole number of decomposed primary CyHP to the total mole number of decomposed tertiary CyHP (hereinafter referred to as "primary/tertiary decomposition molar ratio") was $$4.2 \left( = \frac{16\% \times 0.14 \times 0.56/166}{16\% \times 0.86 \times 0.022/166} \right).$$

The decomposition reaction product containing cuminaldehyde and isopropylbenzyl alcohol, cuminic acid was fed to a stationary tank IV through a pipe 7 and was subjected to oil-water separation again. The water layer was withdrawn from a pipe 9 and a part thereof was supplied to the pipe 2 through a pipe 12 for using it again. In order to maintain the pH value of this water layer to be recycled at 13.7, a 25% aqueous solution of NaOH was supplied to the water layer from a pipe 10. The amount supplied of the aqueous solution was 5 mole % as NaOH based on the amount of CyHP in the oxidation product. The remainder of the water layer withdrawn through the pipe 9 was discharged from the system through a pipe 11 in an amount corresponding to the amount supplied of the aqueous solution of NaOH.

The oil layers in the stationary tanks II and IV were withdrawn from pipes 4 and 8, respectively, and they were combined and concentrated and the concentrate was acid-decomposed in an acetone solvent in the presence of sulfuric acid as a decomposition catalyst. The primary CyHP content in the concentrated oil layer was 6.8% by weight. The yield of cresol was 97 mole % based on tertiary CyHP.

For comparison, the oily reaction product containing 16% by weight of CyHP and 80% by weight of cymene was acid-decomposed in the same manner as described above except that the treatment with the alkali aqueous solution was not effected. The yield of cresol was 92 mole % based on the tertiary CyHP.

EXAMPLE 2

Procedures of Example 1 were repeated in the same manner except that the extraction temperature was changed to 15° or 40° C. The obtained results, as well as the results obtained in Example 1, are shown in Table 1.

TABLE 1

| Run No. | Extraction Temperature (°C.) | Heating Time (minutes) | Total Primary CyHP Decomposition Ratio (%) | Total Tertiary CyHP Decomposition Ratio (%) | Primary/ Tertiary Decomposition Molar Ratio |
|---|---|---|---|---|---|
| 1 | 15 | 3 | 50 | 1.7 | 4.8 |
| 2 | 25 | 25 | 56 | 2.2 | 4.2 |
| 3 | 40 | 14 | 52 | 2.7 | 3.0 |

EXAMPLE 3

Procedures of Example 1 were repeated in the same manner except that 100 parts by volume of the oxidation reaction product liquid was extracted with 60 parts of the alkali aqueous solution layer recycled and the decomposition was conducted under heating at 60° C. for 7 minutes. The amount supplied of NaOH was 4 mole % based on the CyHP feed.

The total primary CyHP decomposition ratio was 52%, the total tertiary CyHP decomposition ratio was 1.4%, and the primary/tertiary decomposition molar ratio was 6.1.

EXAMPLE 4

Procedures of Example 1 were repeated in the same manner except that cymene was not fed to the decomposition tank III.

The total CyHP decomposition ratio was 52%, the total tertiary CyHP decomposition ratio was 2.7%, and the primary/tertiary decomposition molar ratio was 3.0.

COMPARATIVE EXAMPLE 1

Figure 2:
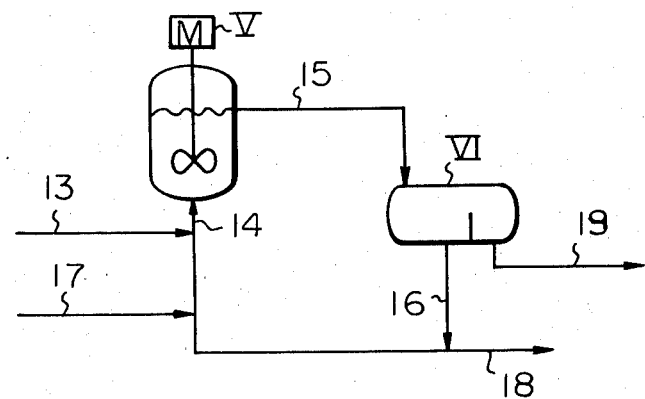
FIG. 2 is a diagram illustrating an example of the conventional apparatus.

The same oily reaction product as used in Example 1, which contained 16% by weight of cymene hydroperoxide (tertiary CyHP/primary CyHP molar ratio=86/14) was treated only by the decomposition without the extraction operation in an apparatus shown in FIG. 2.

The oily reaction product was supplied to a decomposition tank V provided with a stirrer through a pipe 14 and an aqueous solution of sodium hydroxide containing a sodium salt of an organic acid was fed through pipes 17 and 14 to the decomposition tank V. The thermal decomposition was carried out at an oil/water volume ratio of 5/3 and a temperature of 80° C. for 25 minutes. The decomposition product was fed to a stationary tank VI through a pipe 15 to effect oil-water separation. The water layer containing 7.8% of NaOH was returned to the pipe 14 through a pipe 16 and used again for extraction. In order to maintain the pH value of the water layer to be recycled at the predetermined level, a 7% aqueous solution of NaOH was supplied through the pipe 17, and the water layer was withdrawn from a pipe 18 in an amount corresponding to the amount of the supplied aqueous solution of NaOH. The oil layer withdrawn from the stationary tank VI through a pipe 19 was concentrated and acid-decomposed.

The total primary CyHP decomposition ratio was 37%, the total tertiary CyHP decomposition ratio was 4.3%, the primary/tertiary decomposition molar ratio was 1.3, and the yield of cresol was 94%.

What is claimed is:

1. A method of treating hydroperoxide mixtures, which comprises contacting an oily hydroperoxide mixture containing (A) a primary aromatic benzene or naphthalene hydroperoxide having a hydroperoxymethyl group directly bonded to the aromatic benzene or naphthalene nucleus and (B) a tertiary aromatic benzene or naphthalene hydroperoxide having a 2-hydroxyperoxy-2-propyl group bonded directly to the aromatic benzene or naphthalene nucleus with an aqueous alkali solution having a pH value of 12 to 14 thereby to form an aqueous layer wherein the ratio of A/(A+B) in the aqueous layer is higher than the ratio of A/(A+B) in the starting oily mixture and an oily layer wherein the A/(A+B) in the oily layer is lower than the ratio of A/(A+B) in the starting oily mixture, separating the aqueous layer from the oily layer, and decomposing at least a part of the primary aromatic hydroperoxide (A) in the aqueous layer by heating the aqueous layer at a temperature higher than the temperature used for said contacting with the aqueous alkali solution.

2. A method according to claim 1, wherein the oily hydroperoxide mixture is a liquid phase oxidation product of an aromatic compound having a methyl group and an isopropyl group directly bonded to the aromatic benzene or naphthalene nucleus or a conentrate thereof.

3. A method according to claim 1, wherein said contact with the alkali aqueous solution and oil-water separation is carried out at a temperature of 0° to 40° C.

4. A method according to claim 1, wherein decomposition of at least a part of the component (A) is carried out at a temperature of 20° to 80° C., which is higher than the temperature for the contact with the aqueous alkali solution.

5. A method according to claim 1 or 5, wherein decomposition of at least a part of the component (A) is performed under such conditions that the total decomposition ratio of the component (A) is higher than 40% and the total decomposition ratio of the component (B) is lower than 4%.

6. A method according to any of claims 1 or 4, wherein decomposition of at least a part of the component (A) is carried out in the presence of a hydrocarbon.

7. A method according to claim 5 wherein decomposition of at least a part of the component (A) is carried out in the presence of a hydrocarbon.

8. A method according to claim 1 wherein the ratio of the primary aromatic hydroperoxide (A) to the tertiary aromatic hydroperoxide (B) in the starting oily hydroperoxide mixture is from 10/90 to 30/70.

9. A method of treating hydroperoxides which comprises the steps of (i) contacting an oily mixture obtained by liquid phase oxidation of an aromatic benzene or naphthalene compound having methyl and isopropyl groups directly bonded to the aromatic nucleus with molecular oxygen, said mixture containing (A) a primary aromatic benzene or naphthalene hydroperoxide having a hydroperoxymethyl group directly bonded to the aromatic nucleus and (B) a tertiary aromatic benzene or naphthalene hydroperoxide having a 2-hydroperoxy-2-propyl group directly bonded to the aromatic nucleus as an (A)/(B) weight ratio of from 5/95 to 40/60, with an aqueous alkali solution having a pH value of from 12 to 14 at a temperature of from 0° to 40° C., (ii) thereby forming an aqueous layer containing said aromatic hydroperoxides (A) and (B) in such amounts that the ratio of A/(A+B) in said aqueous layer is higher than said ratio in said oily mixture and an oily layer containing said aromatic hydroperoxides (A)

and (B) in such amounts that the ratio of A/(A+B) in said oil layer is lower than said ratio in said oily mixture, (iii) separating the aqueous layer from the oily layer and recovering the oily layer, (iv) adding a hydrocarbon to the separated aqueous layer and decomposing the aqueous layer at a temperature of 20° to 100° C., which is higher than the temperature used for said contacting with the aqueous alkali solution, so that the total decomposition ratio of the primary aromatic hydroperoxide (A) is higher than 40% and the total decomposition ratio of the tertiary aromatic hydroperoxide (B) is lower than 4%, (v) separating the resulting decomposition product into an aqueous layer and an oily layer and recovering the oily layer, and (vi) recycling the separated aqueous layer to step (i).

10. A method according to claim 9, wherein said aromatic compound is cymene and said hydrocarbon is cymene.

11. A method according to claim 9, wherein the alkali aqueous solution is mixed with the oily mixture in an amount of 0.1 to 5 parts by volume per part by volume of the oily mixture.

12. A method according to claim 9, wherein said decomposition is conducted for 0.2 to 100 minutes.

13. A method according to claim 9, wherein the oil layer recovered at the step (iii) is combined with the oil layer recovered at the step (vi) and the mixture is acid-decomposed in acetone.

14. A method according to claim 1 or claim 9 wherein the hydroperoxides (A) and (B) are each monohydroperoxides.

15. A method according to claim 1 or claim 9 wherein the primary aromatic benzene or naphthalene hydroperoxide (A) is a compound selected from the group consisting of

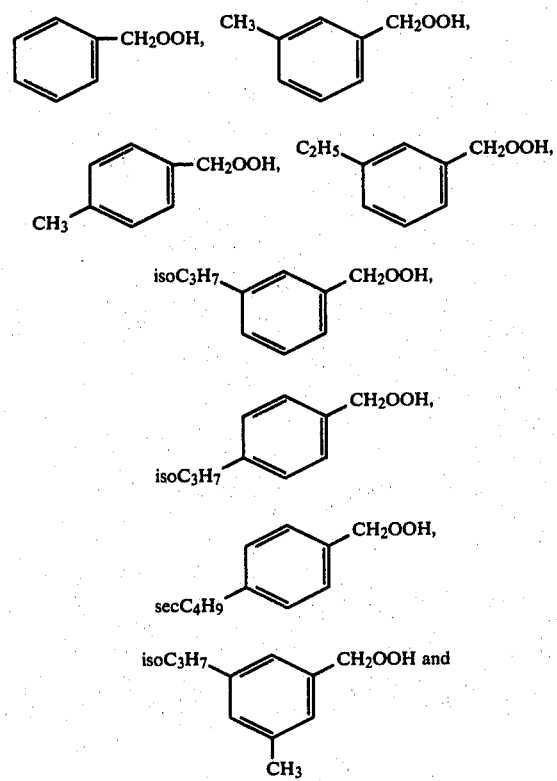

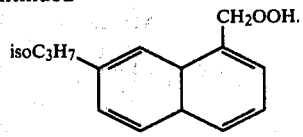

16. The method according to claim 1 or 9 wherein the tertiary aromatic benzene or naphthalene hydroperoxide (B) is a compound selected from the group consisting of

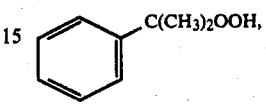

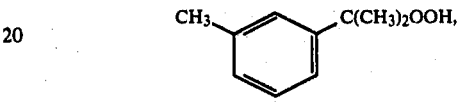

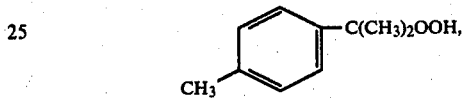

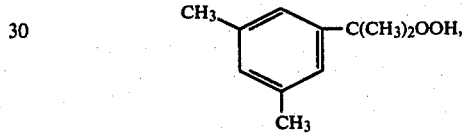

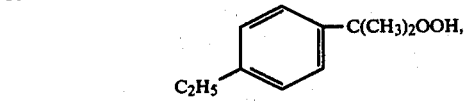

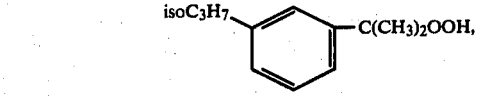

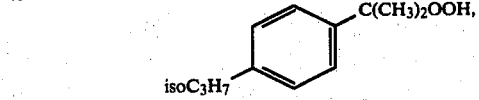

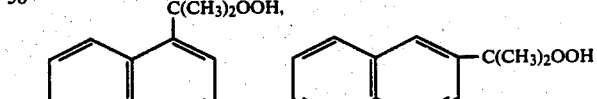

and

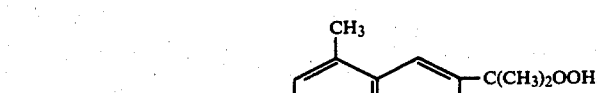

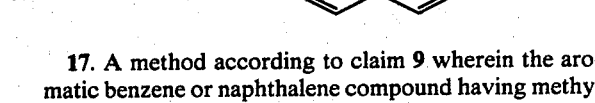

17. A method according to claim 9 wherein the aromatic benzene or naphthalene compound having methyl and isopropyl groups directly bonded to the aromatic nucleus is a compound selected from the group consising of m-cymene, p-cymene, 2,4-dimethylisopropylbenzene, 3,5-dimethylisopropylbenzene and 1-methyl-7-isopropylnaphthalene or a mixture of m-cymene and p-cymene.

18. A method according to claim 17 wherein the starting oily mixture is diluted with said aromatic benzene or naphthalene compound having methyl and isopropyl groups directly bonded to the aromatic nucleus such that the concentration of the hydroperoxides (A) and (B) in said oily mixture is from 1 to 40% by weight.

19. A method according to claim 18 wherein the concentration of the hydroperoxides (A) and (B) in the starting oily mixture is from 5 to 15% by weight.

20. A method according to claim 19 wherein the hydrocarbon added in step (iv) is an aromatic benzene or naphthalene compound which is the same as the aromatic benzene or naphthalene compound in the starting oily mixture.

* * * * *

UNITED STATES PATENT AND TRADEMARK OFFICE
CERTIFICATE OF CORRECTION

PATENT NO. : 4,408,083

DATED : October 4, 1983

INVENTOR(S) : Masakazu Toyoura; Koichi Shomura; Hirotoshi Tsuchida and Tadateru Murakami It is certified that error appears in the above-identified patent and that said Letters Patent is hereby corrected as shown below:

Claim 1, lines 7 and 8 change "2-hydroxyperoxy-2-propyl" to ---2-hydroperoxy-2-propyl---

Claim 9, line 61 change "as" to ---at---.

Signed and Sealed this

Fifteenth Day of May 1984

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,408,083

DATED : October 4, 1983

INVENTOR(S) : Masakazu Toyoura, et al

It is certified that error appears in the above-identified patent and that said Letters Patent is hereby corrected as shown below:

On the title page priority date should read:

-- August 19, 1980 --.

Signed and Sealed this

Seventeenth Day of July 1984

[SEAL]

Attest:

GERALD J. MOSSINGHOFF

Attesting Officer

Commissioner of Patents and Trademarks